(12) United States Patent
Masuda (10) Patent No.: US 9,199,977 B2
(45) Date of Patent: *Dec. 1, 2015

(54) CRYSTAL HAVING CRYSTAL HABITS AND PHARMACEUTICAL COMPOSITION OBTAINED BY PROCESSING THE CRYSTAL

(71) Applicants: POLA PHARMA INC., Tokyo (JP); NIHON NOHYAKU CO., LTD., Tokyo (JP)

(72) Inventor: Takaaki Masuda, Kanagawa (JP)

(73) Assignees: POLA PHARMA INC., Tokyo (JP); NIHON NOHYAKU CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/988,003

(22) PCT Filed: Nov. 2, 2012

(86) PCT No.: PCT/JP2012/079050
§ 371 (c)(1),
(2) Date: May 16, 2013

(87) PCT Pub. No.: WO2014/041708
PCT Pub. Date: Mar. 20, 2014

(65) Prior Publication Data
US 2015/0183766 A1    Jul. 2, 2015

(30) Foreign Application Priority Data
Sep. 14, 2012  (JP) .................................. 2012-202516

(51) Int. Cl.
*C07D 409/06*    (2006.01)
(52) U.S. Cl.
CPC ........... *C07D 409/06* (2013.01); *C07B 2200/13* (2013.01)
(58) Field of Classification Search
CPC .................................................. C07D 409/06
See application file for complete search history.

(56) References Cited

U.S. PATENT DOCUMENTS

| 5,900,488 A * | 5/1999 | Kodama et al. ............ 548/315.1 |
| 2009/0030059 A1 | 1/2009 | Miki et al. |
| 2009/0076109 A1 | 3/2009 | Miki et al. |
| 2009/0137651 A1 | 5/2009 | Kobayashi et al. |
| 2010/0168200 A1 | 7/2010 | Masuda et al. |
| 2010/0173965 A1 | 7/2010 | Masuda et al. |
| 2010/0204293 A1 | 8/2010 | Masuda et al. |
| 2010/0210702 A1 | 8/2010 | Vontz et al. |
| 2012/0022120 A1 | 1/2012 | Kobayashi et al. |
| 2012/0149745 A1 | 6/2012 | Kobayashi et al. |
| 2013/0011351 A2 | 1/2013 | Kobayashi et al. |
| 2013/0090365 A1 | 4/2013 | Kubota et al. |
| 2014/0080882 A1 | 3/2014 | Masuda et al. |

FOREIGN PATENT DOCUMENTS

| EP | 0715856 A1 | 6/1996 |
| EP | 2005958 A1 | 12/2008 |
| JP | 9-100279 A | 4/1997 |
| JP | 2002-114680 A | 4/2002 |
| WO | WO 2007/102241 A1 | 9/2007 |
| WO | WO 2007/102242 A1 | 9/2007 |
| WO | WO 2007/102243 A1 | 9/2007 |
| WO | WO 2009/031642 A1 | 3/2009 |
| WO | WO 2009/031643 A1 | 3/2009 |
| WO | WO 2009/031644 A1 | 3/2009 |
| WO | WO 2010/117091 * | 10/2010 ................. 548/315.1 |
| WO | WO 2014/041825 A1 | 3/2014 |
| WO | WO 2014/041846 A1 | 3/2014 |
| WO | WO 2014/042043 A1 | 3/2014 |
| WO | WO 2014/136282 | 9/2014 |

OTHER PUBLICATIONS

Niwano et al., "Efficacy of NND-502, a novel imidazole antimycotic agent, in experimental models of *Candida albicans* and *Aspergillus fumigatus* infections," *International Journal of Antimicrobial Agents*, vol. 12, pp. 221-228 (1999).

International Search Report and the Written Opinion for International Application No. PCT/JP2012/079050, mailed on Mar. 8, 2013.

U.S. Appl. No. 14/263,293, Masuda et al.

* cited by examiner

*Primary Examiner* — Samantha Shterengarts
(74) *Attorney, Agent, or Firm* — Knobbe, Martens, Olson & Bear, LLP

(57) ABSTRACT

An object is to provide means for improving the solubility of luliconazole. Disclosed is a crystal of luliconazole wherein the crystal has such a crystal habit that (021) plane is a specific crystal growth plane.

5 Claims, 5 Drawing Sheets

Fig. 1

1A Crystal 1

1B Comparative example

CRYSTAL HAVING CRYSTAL HABITS AND PHARMACEUTICAL COMPOSITION OBTAINED BY PROCESSING THE CRYSTAL

CROSS-REFERENCE TO RELATED APPLICATIONS

This application is the U.S. National Phase under 35 U.S.C. §371 of International Application PCT/JP2012/079050, filed Nov. 2, 2012, which claims priority to JP 2012-202516, filed Sep. 14, 2012.

TECHNICAL FIELD

The present invention relates to a crystal of luliconazole having a useful crystal habit as an active pharmaceutical ingredient for pharmaceutical compositions, and pharmaceutical compositions containing the crystal as an active pharmaceutical ingredient.

BACKGROUND ART

Luliconazole is an antifungal agent which is excellent in the action on fungi. At present, luliconazole is widely used as a pharmaceutical or medicine for tinea pedis and tinea corporis, and it is going to be applied also for the action on tinea unguium. In relation to the pharmaceutical preparation (medicament preparation) of luliconazole, it is known as problems which should be solved that luliconazole is converted to stereoisomers, such as the SE isomer and the Z isomer, and that the crystallization of luliconazole is caused immediately after the application (see, for example, Patent Documents 1 to 6). In particular, as for the isomerization, the present inventors have confirmed that the stereoisomerization to the SE isomer or the Z isomer is influenced by components in pharmaceutical preparations, the temperature, and the light. Reflecting the circumstances as described above, a storage condition of 3 weeks at 60° C. is used to evaluate the stability of luliconazole. In this way, it has been necessary that the heating step is shortened as much as possible in the production of luliconazole. However, luliconazole has poor solubility in aqueous media. Therefore, it is required in the formulation of luliconazole that the dissolving step with heating, stirring and other operations is applied. Consequently, it has been demanded to develop any means for improving the solubility of luliconazole and shortening the heating time in the dissolving step. Shortening or reducing the time required in dissolving step has advantages that induce not only the inhibition of the generation or formation of any isomer in this step but also the long-term stabilization obtained by the contribution of lowering the initial value of the isomer amount. In other words, it is affirmed that shortening or reducing the time required in the dissolving step results in the great improvement in the quality.

On the other hand, as for crystals of luliconazole, it is known that the crystals are obtained by recrystallization from a mixture of ethyl acetate and n-hexane (see Patent Document 7). However, nothing is known at all about details of the crystallographic properties such as a crystal system. Further, nothing is known at all about recrystallization from alcohol or the like.

PRECEDING TECHNICAL DOCUMENTS

Patent Documents

Patent Document 1: WO2007/102241;
Patent Document 2: WO2007/102242;
Patent Document 3: WO2007/102243;
Patent Document 4: WO2009/031642;
Patent Document 5: WO2009/031643;
Patent Document 6: WO2009/031644;
Patent Document 7: JP9-100279A.

SUMMARY OF THE INVENTION

Technical Problem

The present invention has been made in the circumstances as described above, an object of which is to provide means for improving the solubility of luliconazole.

Solution to Problem

Taking the foregoing circumstances into consideration, the present inventors have repeatedly performed diligent researches and efforts in order to seek for any means for improving the solubility of luliconazole as an active pharmaceutical ingredient (bulk material). As a result, it has been found out that the solubility as described above can be improved by the modification of crystal habits of luliconazole, and thus the invention has been completed. That is, the present invention resides in the gist or essential characteristics shown below.

<1> A crystal of luliconazole represented by the following formula, wherein the crystal has such a crystal habit that (021) plane is a specific crystal growth plane:

(luliconazole)

<2> The crystal as defined in <1>, wherein $I_{(021)}$ with respect to a sum total of $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ is not less than ⅓, provided that in relation to the diffraction peaks detected in a range of 2θ=5 to 35° in a powder X-ray diffractometry using CuKα radiation, the integrated intensities of the diffraction peaks, which correspond to the (001), (100), (10-1), (011), (110), (11-1), (10-2), (11-2), (020), (021), (20-2), (121), (013), (11-3), and (221) planes, are designated as $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ respectively.

<3> The crystal as defined in <1> or <2>, wherein the crystal has a monoclinic crystal system.

<4> The crystal as defined in any one of <1> to <3>, wherein the crystal is recrystallized from alcohol which may contain water.

<5> A crystal obtained by recrystallizing luliconazole from alcohol which may contain water.

<6> A crystal of luliconazole having such a crystal habit that chlorine atom and nitrogen atom are arranged on a specific crystal growth plane.

<7> An active pharmaceutical ingredient, containing the crystal as defined in any one of <1> to <6>.

<8> A method for producing a pharmaceutical composition, comprising a step of dissolving in a solvent, the crystal as defined in any one of <1> to <6> or the active pharmaceutical ingredient as defined in <7>.

<9> A pharmaceutical composition produced by the production method as defined in <8>.

Advantageous Effects of Invention

According to the present invention, it is possible to provide means for improving the solubility of luliconazole.

DESCRIPTION OF EMBODIMENTS

<1> Crystal of the Present Invention

The crystal of the present invention is a crystal of luliconazole, which is characterized in that the crystal has the crystal habit, wherein the (021) plane is the specific crystal growth plane in relation to the crystal habit. In the case of the crystal of luliconazole, any crystal, which has the crystal habit, is not known. However, the present inventors grasp that various crystals, which have different characteristics, are obtained on account of the difference in the production step of the crystal, for example, the difference in the recrystallization solvent. In order to elucidate the cause thereof, the present inventors have performed the recrystallization by means of changing the recrystallization solvent and performed the powder X-ray diffraction measurements. Parts of the results of the powder X-ray diffraction measurements are shown in the drawings. In any case, the diffraction angles $2\theta$ of the diffraction peaks were coincident with each other, while only the integrated intensities were different from each other. According to this result, the present inventors have judged that the crystals occur, which have different crystal habits each having any difference in relation to the crystal growth plane depending on the recrystallization condition. It has been found out that among the crystals having the different crystal habits as described above, the excellent solubility is induced by the crystal which has such a crystal habit that the integrated intensity of the diffraction peak detected in the vicinity of $2\theta=23°$ corresponding to the (021) plane is specifically large, i.e., the crystal which has such a crystal habit that the (021) plane is the specific crystal growth plane. The excellent solubility shortens or reduces the dissolution time required in the dissolving step, and thus it is possible to suppress the generation or formation of any isomer in the solution.

In this context, the phrase "in the vicinity of $2\theta=23°$" means, for example, a range of $2\theta=23\pm0.5°$.

Figure 6:
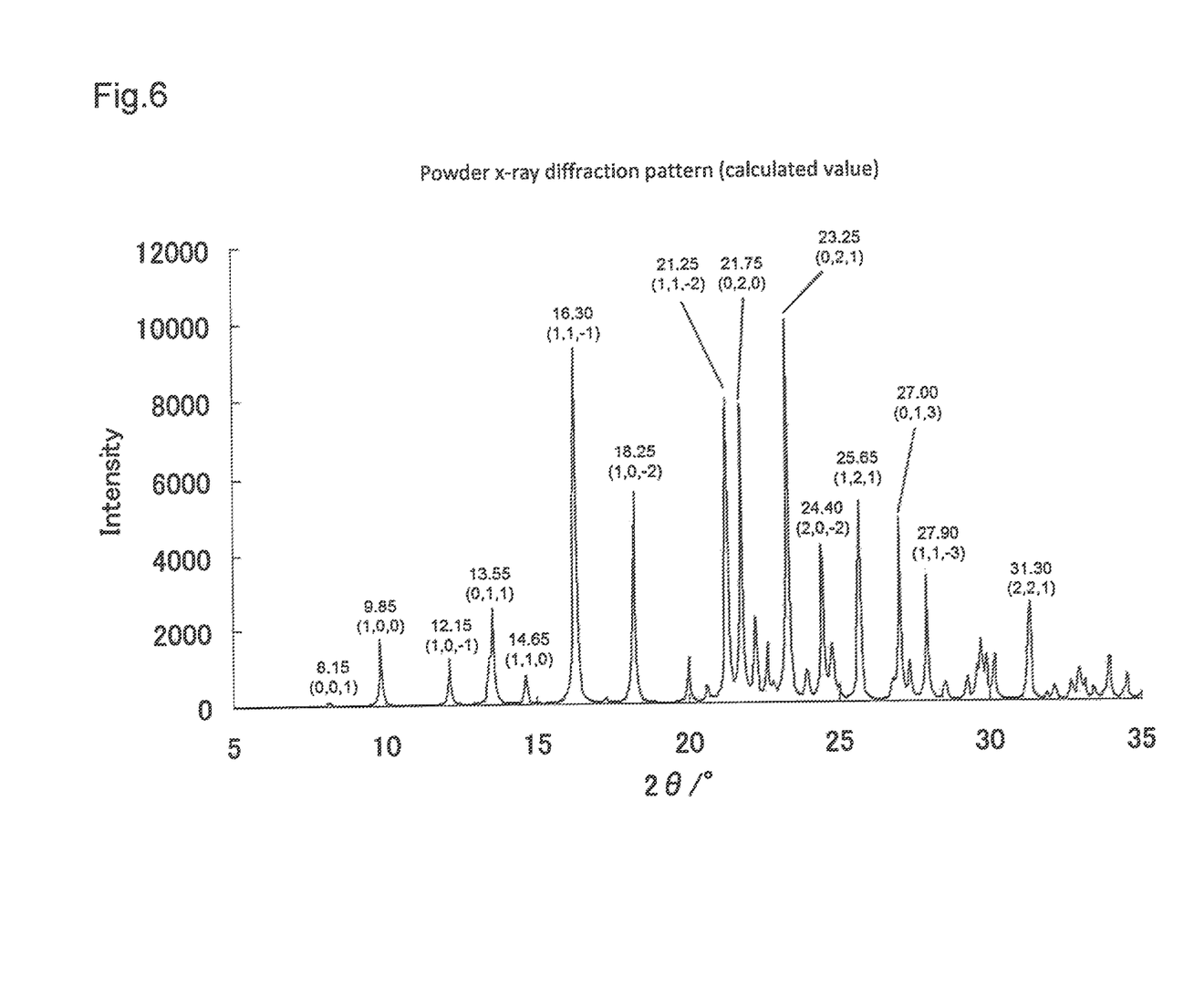
FIG. 6 shows the calculated powder pattern in a range of $2\theta=5$ to $35°$ of the crystal according to the present invention obtained by using the single crystal X-ray diffraction data of luliconazole.

The phrase "diffraction peak detected in the vicinity of $2\theta=23°$ is specifically large" means that "$I_{(021)}$ with respect to a sum total of $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ is not less than $\frac{1}{3}$, provided that in relation to the diffraction peaks detected in a range of $2\theta=5$ to $35°$, the integrated intensities of the diffraction peaks, which correspond to the (001), (100), (10-1), (011), (110), (11-1), (10-2), (11-2), (020), (021), (20-2), (121), (013), (11-3), and (221) planes, are designated as $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ respectively". That is, as shown in Examples described later on, this is because the effect of the present invention has been acknowledged in relation to a integrated intensity ratio of 38%, and it is speculated for the outer edge portion having the equivalent effect that $I_{(021)}$ with respect to the sum total of $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ is not less than $\frac{1}{3}$, provided that the integrated intensities of the diffraction peaks of the (001), (100), (10-1), (011), (110), (11-1), (10-2), (11-2), (020), (021), (20-2), (121), (013), (11-3), and (221) planes are designated as $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ respectively in relation to the diffraction peaks detected in the range of $2\theta=5$ to $35°$. The calculated powder pattern in the range of $2\theta=5$ to $35°$ obtained by using the single crystal X-ray diffraction data of luliconazole is shown in FIG. 6.

The crystal as described above is obtained by recrystallization utilizing an alcohol, which may contain water, as the recrystallization solvent. Those preferably usable as the alcohol described above include alcohols each having a number of carbon atom or atoms of 1 to 4 (methanol, ethanol, 1-propanol (propyl alcohol), 2-propanol (isopropyl alcohol), 1-butanol (n-butyl alcohol), 2-butanol (sec-butyl alcohol), 2-methyl-1-propanol (isobutyl alcohol), and 2-methyl-2-propanol (tert-butyl alcohol)). More preferably, it is possible to exemplify, for example, ethanol, isopropyl alcohol, and normal butyl alcohol. Much more preferably, the alcohol is ethanol. Of course, it is also possible to mix two or more alcohols selected from the alcohols described above and use the mixture as the recrystallization solvent. The alcohol as described above may be used together with water upon the use.

Alternatively, the alcohol may be used in a state of being previously hydrated or allowed to contain water. The amount of water, which can be used together, is preferably exemplified, for example, by 30 to 80%, 50 to 75%, or about 70% at the maximum with respect to the total amount of alcohol which may contain water.

As for the recrystallization, it may be performed with a water-containing alcohol. Alternatively, it is also possible to make water the use as a poor solvent. It means that enough amount of water for deposition may be added to the alcohol solution of luliconazole. From a viewpoint of the purity, it is possible to exemplify such a preferred mode that the recrystallization is performed with an alcohol containing 10% water. When the recrystallization is performed under the condition as described above, it is possible to obtain the crystal having the desired crystal habit with good reproducibility or repeatability.

The recrystallization can be performed in accordance with any ordinary recrystallization technique.

<2> Active Pharmaceutical Ingredient of the Present Invention

The crystal of the present invention thus obtained has the excellent solubility, for the following reason. That is, it is considered that the group, which has the affinity for the solvent, is oriented on the specific crystal growth plane of the crystal habit. The crystal of the present invention has the feature as described above, and hence the crystal of the present invention is especially preferred to be used as the active pharmaceutical ingredient (bulk material) for the pharmaceutical preparation of luliconazole which is produced by such a production method that the heating and dissolving step is reduced or decreased as much as possible, in view of the stability of luliconazole to be secured. When the crystal of the present invention is used as the active pharmaceutical ingredient for the pharmaceutical preparation of luliconazole, for example, the grinding or pulverization can be also performed to adjust the particle size (grain size) within a range in which the crystal habit of the crystal of the present invention is not damaged. When the pharmaceutical preparation is manufactured by using the crystal of the present invention, then it is possible to shorten the heating time required in the formulation, and thus it is possible to suppress the amount of generation or formation of any isomer to be low in the pharmaceutical preparation after the production. When the amount of generation of any isomer is suppressed, it is also possible to improve the time-dependent stability.

The active pharmaceutical ingredient of the present invention can contain substances, impurities, and isomers within a range of being permitted as the active pharmaceutical ingredient, other than the crystal of luliconazole. However, it is especially preferred to adopt a form substantially consisting of the crystal of luliconazole.

<Diffraction Peak at 2θ=23° in Powder X-Ray Diffraction Pattern>

The crystal habit of the crystal of the present invention is characterized by the diffraction peak at 2θ=23° in the powder X-ray diffraction pattern. The peak at 2θ=23° in the powder X-ray diffraction pattern has been theoretically calculated by using the single crystal X-ray diffraction data. As a result, the peak represents the (021) plane. Two chlorine atoms and a nitrogen atom belonging to cyano group are arranged on this plane. On the contrary, in the case of the crystal which is recrystallized from n-hexane/ethyl acetate as the crystal having been hitherto known, the crystal has such a crystal habit that the (11-1) plane is the specific crystal growth plane, wherein carbon atoms belonging to phenyl group are arranged on this plane. This plane is the plane represented by the diffraction peak of 2θ=16° in the powder X-ray diffraction pattern.

<3> Pharmaceutical Preparation of Luliconazole of the Present Invention

The pharmaceutical preparation of luliconazole of the present invention is characterized in that the crystal, which has such a crystal habit that the (021) plane is the specific crystal growth plane, is contained. The crystal as described above is excellent in the solubility in the solvent such as ethanol or the like. Therefore, it is preferable to adopt the pharmaceutical preparation which is produced by the production step that includes the dissolving step. Specifically, it is possible to preferably exemplify, for example, a pharmaceutical solution, a pharmaceutical emulsion, and a pharmaceutical ointment of the liquid droplet dispersion type. In particular, the pharmaceutical preparation, in which the content of luliconazole exceeds 5% by mass, requires a considerable period of time to perform the dissolving step. Therefore, the pharmaceutical preparation of luliconazole of the present invention is preferred in view of the shortening or reducing the time. The preferred content of luliconazole is 0.1 to 30% by mass with respect to the total amount of the pharmaceutical preparation. More preferably, the content of luliconazole is 0.5 to 15% by mass. Of course, when luliconazole is processed into an oral administration agent such as a tablet or the like, the rate of dissolution is excellent, which is preferred. The pharmaceutical preparation for oral administration as described above also belongs to the pharmaceutical preparation of the present invention.

The time required for the dissolving step, which is required when the crystal having such a crystal habit that the (021) plane of luliconazole crystals is the specific crystal growth plane is used in the dissolving step to prepare, for example, a pharmaceutical preparation in which the content of luliconazole is 0.1 to 30% by mass with respect to the total amount of the pharmaceutical preparation, may be not more than 80%, preferably not more than 75%, and more preferably not more than 70% as compared with the time which is required for the dissolving step when the crystal having such a crystal habit that the (11-1) plane is the specific crystal growth plane is used. Although the time required for the dissolving step depends on, for example, the processing condition (treatment condition) and the content of luliconazole in the pharmaceutical preparation as well.

The pharmaceutical preparation of the present invention can be produced by performing the process or treatment in accordance with any ordinary method while appropriately adding thereto, for example, solvent, coloring agent, antioxidant, chelating agent, emulsifier/dispersing agent, solubilizing agent, disintegrating agent, excipient, binding agent, coating agent, and taste/odor-correcting agent other than the luliconazole crystal having such a crystal habit that the (021) plane is the specific crystal growth plane.

The pharmaceutical preparation of luliconazole of the present invention obtained as described above is characterized in that the amounts of isomers are suppressed in relation to the initial values obtained immediately after the production of luliconazole. The amounts of isomers (SE isomer, Z isomer), which are obtained in relation to the initial values provided immediately after the production of luliconazole, may be as follows as compared with the case in which the crystal having such a crystal habit that the (11-1) plane is the specific crystal growth plane is used. That is, for example, in the case of the SE isomer, the amount of isomer may be not more than 80%, preferably not more than 70%, and more preferably not more than 60%. In the case of the Z isomer, the amount of isomer may be not more than 70%, preferably not more than 60%, and more preferably not more than 50%. In the case of the sum of those of the SE isomer and the Z isomer, the sum may be not more than 80%, preferably not more than 70%, and more preferably not more than 60%.

The pharmaceutical composition of the present invention is preferably used to treat or cure the disease caused by any fungus or prevent the deterioration of the disease by utilizing the characteristic of luliconazole. The disease caused by any fungus can be exemplified by tinea pedis such as athlete's foot, tinea corporis such as candidiasis and tinea versicolor, and trichophytosis of hard keratin portion such as tinea unguium. It is especially preferable to use the pharmaceutical composition of the present invention for treating the disease of the hard keratin portion such as tinea unguium, because the effect thereof is remarkable. The effect of the pharmaceutical composition of the present invention is expressed on the nail especially preferably. However, the effect is also exerted on any ordinary dermatomycosis. Therefore, the pharmaceutical composition, which is directed to the dermatomycosis and which fulfills the construction of the present invention, also belongs to the technical scope of the present invention. The dermatomycosis as described above can be exemplified, for example, by the tinea pedis and the trichophytosis of the propagation in horny substance type appearing, for example, in the heel and being included in the tinea pedis. As for the dermatomycosis described above, it is preferable to make the application to the trichophytosis of the propagation in horny substance type on which any ordinary agent or drug hardly exerts the effect, because the effect of the present invention remarkably arises.

The mode of use can be appropriately selected while considering, for example, the body weight, the age, the sexuality, and the symptoms or condition of the patient. However, in the case of an adult, it is preferable to administer luliconazole in an amount of 0.01 to 1 g per day in ordinary cases. Reference can be made to the amount of use of luliconazole ordinarily used for the disease caused by any fungus.

For example, in the case of any preparation for external use, it is possible to exemplify the application in an appropriate amount to the disease portion once or several times a day. It is preferable that the treatment as described above is performed every day. In particular, in the case of the tinea unguium, luliconazole as the active ingredient, which is in an amount that cannot be brought about by any ordinary pharmaceutical preparation, can be transferred into the nail. Accordingly, the tinea unguium can be cured by means of only the external administration without taking or orally administering any antifungal agent for a long period of time. Further, the recurrence and the reinfection cause great problems in relation to the tinea unguium. However, it is possible to avoid the recurrence and the reinfection as described above by administering the pharmaceutical composition of the present invention for 1 week to 2 weeks after the quietness of symptoms. In such a mode, the pharmaceutical composition of the present invention has the preventive effect.

EXAMPLES

The present invention will be explained in further detail below as exemplified by Examples. However, the present invention is not limited to Examples described below.

Example 1

Ethanol containing 10% water was added to luliconazole, followed by being heated, stirred, and filtrated while applying the heat. A filtrate was quickly cooled with an ice bath and the wall surface was scraped with a spatula to perform the recrystallization. Crystals were collected by filtration, followed by being dried by using phosphorus pentaoxide to obtain Crystal 1 of the present invention. In distinct Comparative Example, the same process or treatment was performed while replacing the solvent with a mixture of ethyl acetate/n-hexane (5:1) to obtain Crystal of Comparative Example. The elution or dissolution test was performed for the two types of the crystals to investigate the elution or dissolution profile. After confirming the dissolution of all crystals, the Z isomer and the SE isomer, which were the isomers generated or formed in the solution, were analyzed and quantitatively measured by HPLC assay.

In the elution or dissolution test, 500 mL of anhydrous ethanol was used as the solvent, and 1 g of luliconazole was dissolved under constant stirring at room temperature. The time, which was required for the dissolution, was simultaneously measured. Results are shown in Table 1. According to Table 1, it is appreciated that the time required for the dissolution is short for Crystal 1, and thus the generation of the Z isomer and the SE isomer as the isomers is suppressed in the dissolving step.

The condition for HPLC was as follows. Column: CHIRALCEL OD-RH 4.6×150 mm, column temperature: 35° C., mobile phase: mixture of methanol/2% aqueous solution of potassium hexafluorophosphate (85:15, v/v), flow rate: 0.6 mL/min., detection: 295 nm).

(Z isomer)

(SE isomer)

TABLE 1

| Sample | Time required until dissolution (minutes) | Amount of generation of Z isomer (%) | Amount of generation of SE isomer (%) |
|---|---|---|---|
| Crystal 1 | 200 | 0.06 | 0.06 |
| Crystal of Comp. Ex. | 300 | 0.13 | 0.09 |

Figure 1:
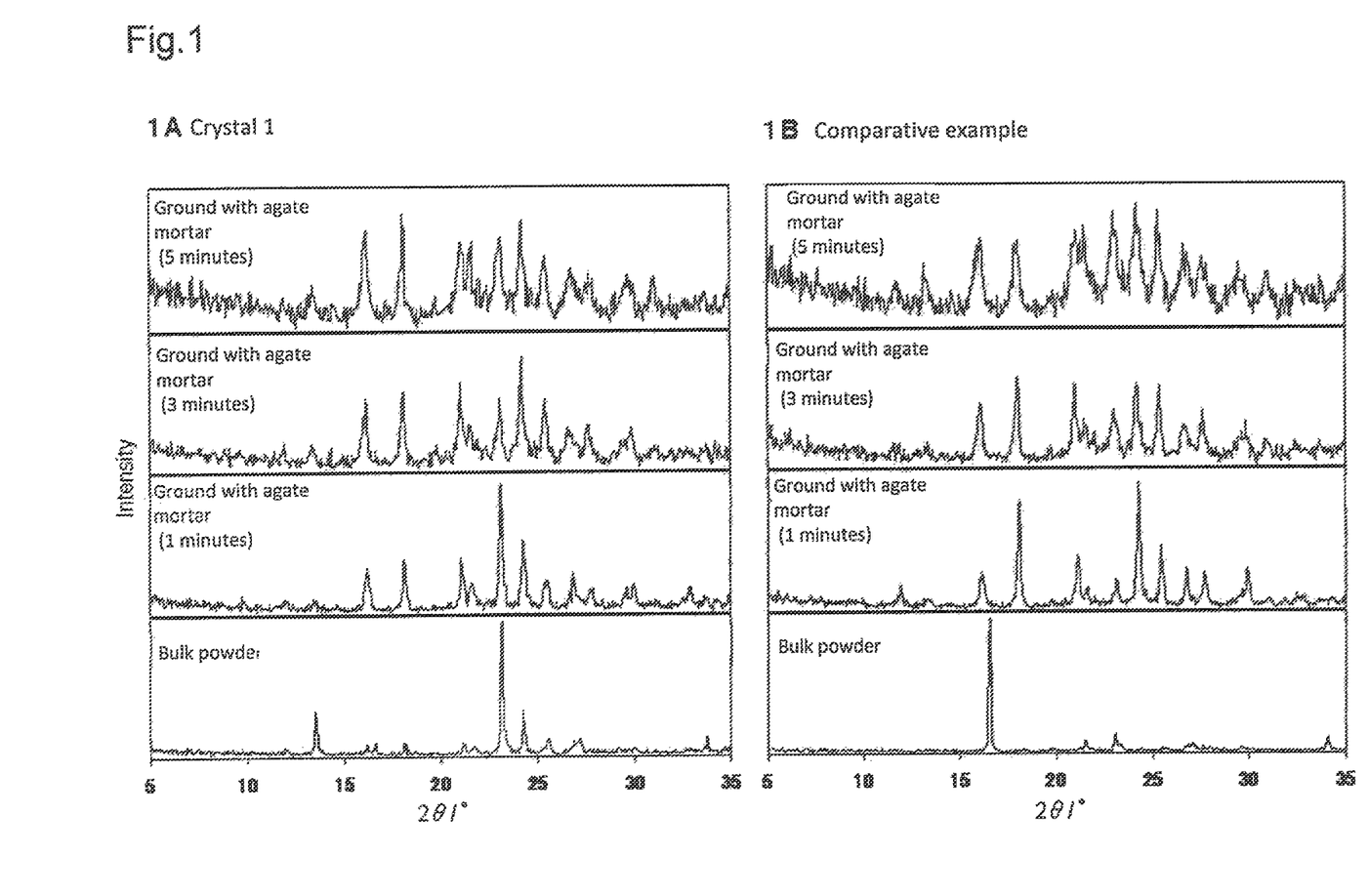
FIG. 1 shows results of the powder X-ray diffraction measurements. Panel A shows results of the powder X-ray diffraction measurements performed for crystals of the present invention and for materials obtained after grinding or pulverizing the crystal. Panel B shows results of the powder X-ray diffraction measurements performed for crystals of Comparative Example and for materials obtained after grinding or pulverizing the crystal.

The powder X-ray diffraction measurement was performed for Crystal of Comparative Example and Crystal 1 of the present invention (name of machine type of apparatus: XRD-DSC II, name of manufacturer: Rigaku Corporation, Condition: X-ray source: CuKα, measurement temperature: room temperature, tube voltage: 40 kV, tube amperage: 40 mA, 2θ: 5 to 35°, step angle: 0.05°). Obtained results are shown in FIG. 1. According to FIG. 1, it is appreciated that the diffraction peak of 2θ=23° is specifically large in the case of Crystal 1 of the present invention, while the diffraction peak of 2θ=16° is specifically large in the case of Crystal of Comparative Example. Further, the diffraction angles of all of the diffraction peaks were coincident with each other. Accordingly, it is appreciated that the two crystals have the same crystal form, but they are different in the crystal habit.

Each of Crystal of the Comparative Example and Crystal 1 of the present invention was ground or pulverized with an agate mortar to perform the powder X-ray diffraction measurements. Results are shown in FIG. 1. As a result of the grinding, the specific crystal growth plane is destroyed, the integrated intensities of the diffraction peaks are uniformized, and the both patters are approximate to one another as well. It has been clarified that the crystal habit differs therebetween.

Figure 2:
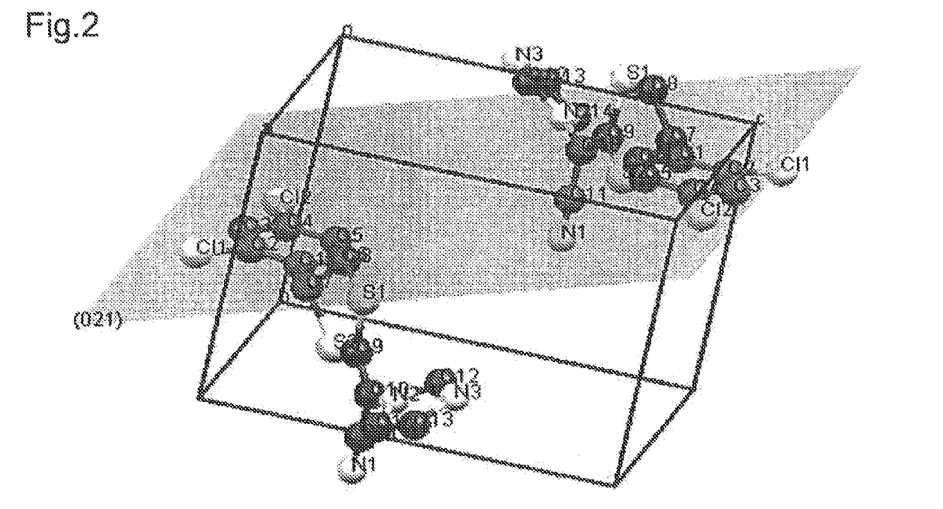
FIG. 2 shows the packing diagram obtained by using the single crystal X-ray diffraction data of luliconazole for a crystal having such a crystal habit that the (021) plane is a specific crystal growth plane.
Figure 3:
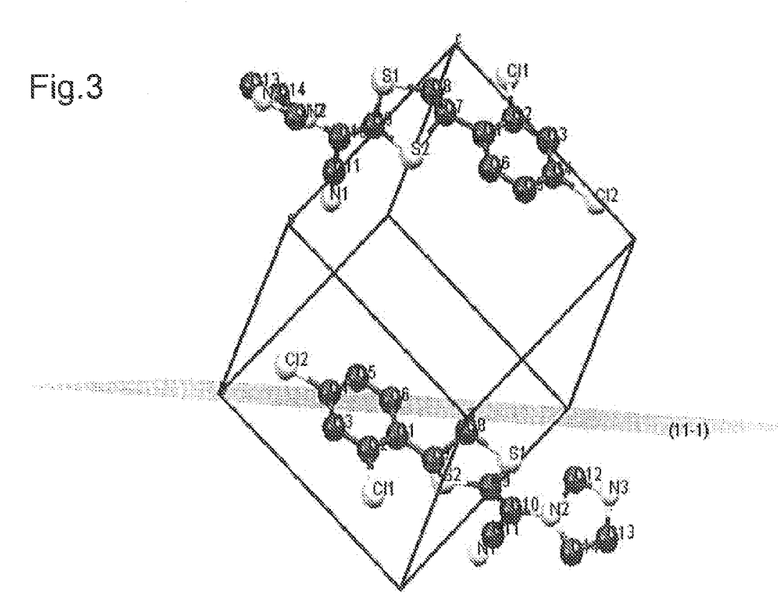
FIG. 3 shows the packing diagram obtained by using the single crystal X-ray diffraction data of luliconazole for a crystal having such a crystal habit that the (11-1) plane is a specific crystal growth plane.

The single crystal X-ray structure analysis was performed for luliconazole (name of machine type of apparatus: RU-H2R, name of manufacturer: Rigaku Corporation, Condition: X-ray source: CuKα, measurement temperature: 26° C., tube voltage: 50 kV, tube amperage: 180 mA, 2θmax: 150.0°, structure analysis method: direct method (SHELX 86)). On the basis of the data, the comparison was made with the data of the powder X-ray diffraction measurements of Crystal 1 of the present invention to specify the specific crystal growth plane. The single crystal, which was used for the single crystal X-ray structure analysis, was obtained by recrystallization three times from ethanol by using the crystal having been obtained by recrystallization from a mixture of n-hexane/ethyl acetate. According to the analysis value obtained from the single crystal X-ray structure analysis, it has been revealed that the peak of 2θ=23° in the powder X-ray diffraction pattern indicates the (021) plane (name of software: Mercury). Further, it has been revealed that the diffraction peak of 2θ=16° indicates the (11-1) plane. Further, the crystal system was a monoclinic. The drawings, each of which illustrates the crystal structure and the specific crystal growth plane determined by the calculation, are shown in FIGS. 2 and 3. Accordingly, it is estimated that the chlorine atoms and the nitrogen atom are arranged on the (021) plane, and thus the excellent solubility in ethanol is obtained. The crystal system, the space group, the lattice constant, and the R factor were as follows.

Crystal system: Monoclinic
Space group: $P2_1$
Lattice constant:
a=9.0171 (9)Å
b=8.167 (1)Å
c=10.878 (1)Å
β=95.917 (9)°
R factor:
R=0.046
$R_w$=0.047

Example 2

Figure 4:
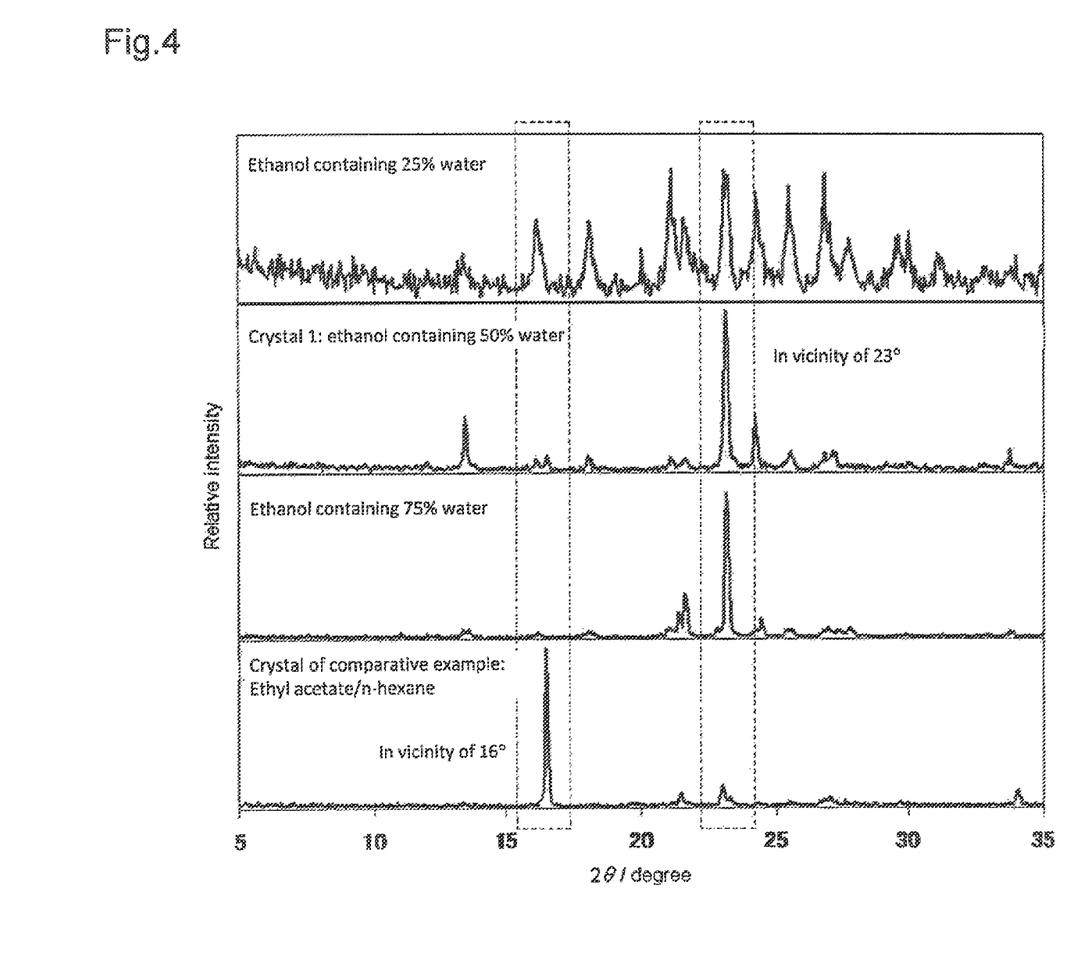
FIG. 4 shows results of the powder X-ray diffraction measurements performed for crystals manufactured by using recrystallization solvents in each of which the ratio is changed.

In order to investigate the reproducibility of the crystal habit in relation to the recrystallization condition, the recrystallization was performed while changing the recrystallization solvent, to perform the powder X-ray diffraction measurements for the obtained crystals. Results are shown in Table 2 and FIG. 4. Accordingly, it is appreciated that the crystal of the present invention is obtained by recrystallization from alcohol which may contain water. It is also appreciated that the content of water is preferably not less than 50% in this case. Further, it is also appreciated that the integrated intensity of 2θ=23° is preferably not less than ⅓ of the sum total of that of main peaks.

TABLE 2

| Recrystallization solvent | Main peak | Integrated intensity ratio | Solubility |
|---|---|---|---|
| Ethanol containing 25% water | 23 (2θ/°) | 11% | solubility is not so satisfactory |
| Ethanol containing 50% water | 23 (2θ/°) | 38% | solubility is satisfactory |
| Ethanol containing 75% water | 23 (2θ/°) | 48% | solubility is satisfactory |

Example 3

A pharmaceutical preparation of luliconazole having the following formulation was manufactured by using Crystal 1 of the present invention to quantitatively measure isomers immediately after the manufacturing. The manufacturing was performed such that the following formulation was heated and solubilized with a water bath, followed by being stirred and cooled. The time required for the dissolution was not more than 5 minutes. The content of the Z isomer thereof was not more than the detection limit, and the content of the SE isomer was 0.03%. Accordingly, it has been confirmed that the dissolving operation can be quickly completed by using the crystal of the present invention, and thus the generation of any isomer can be suppressed in the production steps.

TABLE 3

| Component | % by mass |
|---|---|
| Luliconazole | 1 |
| N-methyl-2-pyrrolidone | 8 |
| Diisopropyl adipate | 5 |
| 1,3-Butanediol | 30 |
| Water | 30 |
| Ethanol | 26 |

Example 4

The melting point was measured by using a thermogravimetric/differential thermal analysis (TG/DTA) (name of machine type of apparatus: TG 8120, name of manufacturer: Rigaku Corporation).

Figure 5:
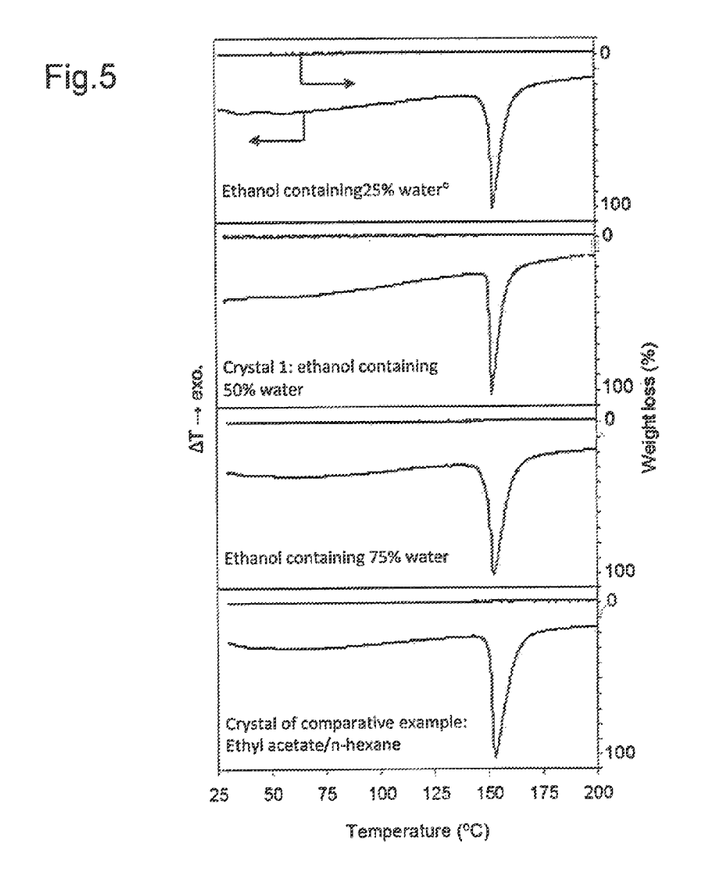
FIG. 5 shows TG/DTA curves in Example 4.

Results are shown in Table 4 and FIG. 5. No peak was observed at any temperature other than the melting point. The crystals were not solvated crystalline forms as well. It was estimated that the crystal forms were same each other.

TABLE 4

| <Melting Point (Onset Temperature)> | |
|---|---|
| Ethanol containing 25% water | 151.1° C. |
| Crystal 1 (ethanol containing 50% water) | 150.5° C. |
| Ethanol containing 75% water | 149.8° C. |
| Ethyl acetate/n-hexane | 149.9° C. |

INDUSTRIAL APPLICABILITY

The present invention can be applied to the pharmaceutical.

What is claimed is:

1. A crystal of luliconazole represented by the following formula, wherein the crystal is recrystallized from alcohol which optionally contains water, wherein the crystal has such a crystal habit that (021) plane is a specific crystal growth plane:

(luliconazole)

2. The crystal according to claim 1, wherein $I_{(021)}$ with respect to a sum total of $I_{(001)}$, $I_{(100)}$, $I_{(10\text{-}1)}$, $I_{(011)}$, $I_{(110)}$, $I_{(11\text{-}1)}$, $I_{(10\text{-}2)}$, $I_{(11\text{-}2)}$, $I_{(020)}$, $I_{(021)}$, $I_{(20\text{-}2)}$, $I_{(121)}$, $I_{(013)}$, $I_{(11\text{-}3)}$, and $I_{(221)}$ is not less than ⅓, provided that in relation to the diffraction peaks detected in a range of 2θ=5 to 35° in a powder X-ray diffractometry using CuKα radiation, the integrated intensities of the diffraction peaks, which correspond to the (001), (100), (10-1), (011), (110), (11-1), (10-2), (11-2), (020), (021), (20-2), (121), (013), (11-3), and (221) planes, are designated as $I_{(001)}$, $I_{(100)}$, $I_{(10\text{-}1)}$, $I_{(011)}$, $I_{(110)}$, $I_{(11\text{-}1)}$, $I_{(10\text{-}2)}$, $I_{(11\text{-}2)}$, $I_{(020)}$, $I_{(021)}$, $I_{(20\text{-}2)}$, $I_{(121)}$, $I_{(013)}$, $I_{(11\text{-}3)}$, and $I_{(221)}$ respectively.

3. The crystal according to claim 1, wherein the crystal has a monoclinic crystal system.

4. An active pharmaceutical ingredient, containing the crystal as defined in claim 1.

5. A method for producing a pharmaceutical composition, comprising a step of dissolving, in a solvent, the crystal as defined in claim 1.

* * * * *

UNITED STATES PATENT AND TRADEMARK OFFICE
CERTIFICATE OF CORRECTION

PATENT NO.        : 9,199,977 B2
APPLICATION NO.   : 13/988003
DATED             : December 1, 2015
INVENTOR(S)       : Takaaki Masuda It is certified that error appears in the above-identified patent and that said Letters Patent is hereby corrected as shown below:

In the claims
In column 11 at line 13 (approx.), In Claim 2, change "$I_{(021)}$)" to --$I_{(021)}$--.

Signed and Sealed this
Twenty-eighth Day of June, 2016

Michelle K. Lee
*Director of the United States Patent and Trademark Office*